(12) United States Patent
Loboda

(10) Patent No.: US 6,630,662 B1
(45) Date of Patent: Oct. 7, 2003

(54) SETUP FOR MOBILITY SEPARATION OF IONS IMPLEMENTING AN ION GUIDE WITH AN AXIAL FIELD AND COUNTERFLOW OF GAS

(75) Inventor: Alexandre V. Loboda, North York (CA)

(73) Assignee: MDS Inc., Concrod (CA)

( * ) Notice: Subject to any disclaimer, the term of this patent is extended or adjusted under 35 U.S.C. 154(b) by 0 days.

(21) Appl. No.: 10/128,528

(22) Filed: Apr. 24, 2002

(51) Int. Cl.⁷ .................................................. H01J 49/40
(52) U.S. Cl. ....................... 250/281; 250/282; 250/290
(58) Field of Search ................................ 250/281, 282, 250/290, 292

(56) References Cited

U.S. PATENT DOCUMENTS 5,487,386 A    1/1996   Wakabayashi et al.
6,512,226 B1 *  1/2003  Loboda et al. ............... 250/282

OTHER PUBLICATIONS

Howard R. Morris et al, High Sensitivity Collisionally–activated Decomposition Tandem Mass Spectrometry on a Novel Quadrupole/Orthogonal–acceleration Time–of–Flight Mass Spectrometer, Rapid Communications in Mass Spectrometry, vol. 10, 889–896 (1996).

Andrej Shevchenko et al, Rapid "de Novo" Peptide Sequencing by a Combination of Nanoelectrospray, Isotopic Labeling and a Quadrupole/Time–of–flight Mass Spectrometer, Rapid Communications in Mass Spectrometry, vol. 11, 1015–1024 (1997).

* cited by examiner

Primary Examiner—Kiet T. Nguyen
(74) Attorney, Agent, or Firm—Bereskin & Parr

(57) ABSTRACT

To control movement of ions in a mass spectrometer, an ion guide has means for generating an electric field along the ion guide, and also provision for generating a gas flow along the ion guide. This then subjects ions to forces, an electric field force and a drag force. These can be set to control motion of ions as desired. The ion guide can form part of ion mobility section, in which case the forces can be set to enhance separation of ions and to control elution of different groups of ions from the ion mobility spectrometer for subsequent analysis. Eluted ions can be selected to further analysis, e.g., collisional fragmentation followed by mass analysis in a time-of-flight instrument. The technique is applicable to other elements of a mass spectrometer; for example, the fragmentation cell can be configured so that ions therein are subjected to both drag forces and electric forces, to control movement thereof.

29 Claims, 6 Drawing Sheets

SETUP FOR MOBILITY SEPARATION OF IONS IMPLEMENTING AN ION GUIDE WITH AN AXIAL FIELD AND COUNTERFLOW OF GAS

FIELD OF THE INVENTION

This invention relates to a method of and an apparatus for separating ions based on their mobility in a gas. More particularly, the invention is based on counteraction of forces from an axial electric field and drag of the gas flow. The invention is intended to improve the resolution of mobility separation and to facilitate coupling of a mobility separation stage to a mass spectrometer

BACKGROUND OF THE INVENTION

Mobility separation, also known as ion mobility separation, can be a useful method on its own or in combination with mass spectrometry. Mobility separation is widely used nowadays, but it suffers from some drawbacks. Firstly, mobility separation is a relatively low resolution technique; typical resolution ranges from 10 to 300. Another significant drawback is low efficiency. Ion transmission can be poor due to diffusion spreading of the ion beam as well as due to low duty cycle in sampling. Diffusion spreading can become an important problem if a mobility separation stage needs to be coupled to a mass spectrometer. The duty cycle inefficiency arises, since once a packet of ions is introduced into the drift tube of an ion mobility spectrometer, no further ions can be introduced until the first packet of ions has completely cleared the drift tube.

In many ion mobility spectrometers, the residence time is relatively short (e.g., 1–10 milliseconds) so that diffusion spreading is not significant. It can be allowed for by providing a detector with a suitably large capture area, to accept a wide beam.

One of the ways to overcome diffusion spreading is described in U.S. Pat. No. 5,487,386 and assigned to the assignee of the present invention. This patent describes an ion guide with an axial field setup or arrangement, where radial confinement is accomplished in the ion guide and mobility separation can occur along the axis, due to effect of the axial field. Still, this setup or arrangement suffers from diffusion along the axis that causes significant peak broadening and thus low resolution, with a resolution of around 10 being obtained with practical parameters. A longer ion guide and higher operating pressure allow a higher resolution to be obtained, but there are practical limits to the length and operating pressure of the ion guide. Losses due to the low duty cycle can be eliminated in this setup by using ion accumulation upstream in a dedicated trap or in a portion of the ion guide that is acting as a trap.

SUMMARY OF THE INVENTION

The present invention is based on the realization that a significant improvement can be obtained if an in guide with an axial field is combined with a counter flow of gas to carry out mobility separation. More particularly, the invention is based on the observation that there are then two forces available to drive ions along the axis of the ion guide filled with gas: the axial electric field and the drag of the gas flow. When the forces are equal and act on the ions in opposite directions, the ion position will be virtually stationary. The radial motion is confined by RF forces, and thus the ions can reside or be trapped inside the ion guide for an extended period of time, without significant losses. The ions then can be moved in one direction or another by a small change in one of the axial forces.

A further important consideration is that by applying counteracting forces, which in the limit could balance one another, ion residence times become much larger. Residence times, practically, are limited by depopulation due to chemical reaction, which in turn depends on preventing impurities being present. Residence times could be of the order of seconds.

As the magnitude of each force is specific for each type of ion, this counteraction effect can be used for separation. Mobility characteristics vary widely and can thus offer more opportunities for separating ions. The present invention selects the ions based, at least in part, on their mobility coefficients. Indeed, when two forces balance each other, it means that the velocity of the ion through the gas, in the axial direction, caused by the electric field matches the velocity of the gas flow. For a fixed velocity of the gas flow, flowing from the exit towards the inlet of the ion guide, the ions will be extracted slightly above the point where their mobility coefficient is sufficient to create the same ion velocity under the applied electric field.

The present inventor has also realized that numerous practical arrangements or setups can be developed from the basic principle. One characteristic differentiating the various arrangements is the direction of the gas flow. An arrangement will be called "forward" when the gas flow is directed away from the inlet of an ion guide to its exit; and correspondingly will be called "backward" when the gas flow directed from the exit towards the inlet of the ion guide. The magnitude of either the electrical field force of the gas drag force and be varied to accomplish separation. Each of the forces can in general have a nonlinear profile along the axis to optimize separation.

In accordance with the first aspect of the present invention, there is provided a method of separating ions, the method comprising:

a) supplying ions to a radio frequency ion guide;

b) applying an axial electric field to provide a force in one direction along the axis of the ion guide; and c) providing a gas flow along the ion guide to provide a drag force on ions opposing the force provided by the electric field.

While it is preferred to use a radio frequency ion guide, for some purposes, it is anticipated that the invention could be implemented using other ion guides. Accordingly, another aspect of the present invention provides a method of separating ions, the method comprising:

(a) supplying ions to an ion guide;

(b) applying an axial electric field to provide a force in one direction along the axis of the ion guide;

(c) providing a gas flow along the ion guide to provide a drag force on ions opposing the force provided by the electric field; and (d) initially setting the electric field and the gas flow such that for at least some ions the force of the electric field and the drag force provided by the gas flow balance one another, to retain the ions within the ion guide, and subsequently adjusting at least one of the electric field and the gas flow to cause desired ions to elute from the ion guide.

A further aspect of the present invention provides an apparatus for separating ions, the apparatus comprising:

an ion guide;

means for generating an electric field along the length of the ion guide; and means for supplying gas to at least one location of the ion guide and for exhausting gas from at least one other location of the ion guide, to generate a desired gas velocity profile along the ion guide, whereby, in use, movement of ions along the ion guide is dependent upon both an electric field force and a drag force applied to the ions.

BRIEF DESCRIPTION OF THE DRAWINGS

For a better understanding of the present invention and to show more clearly how it may be carried into effect, reference will now be made, by way of example, to the accompanying drawings, which show embodiments of the invention and in which.

DETAILED DESCRIPTION OF THE INVENTION

Figure 1:
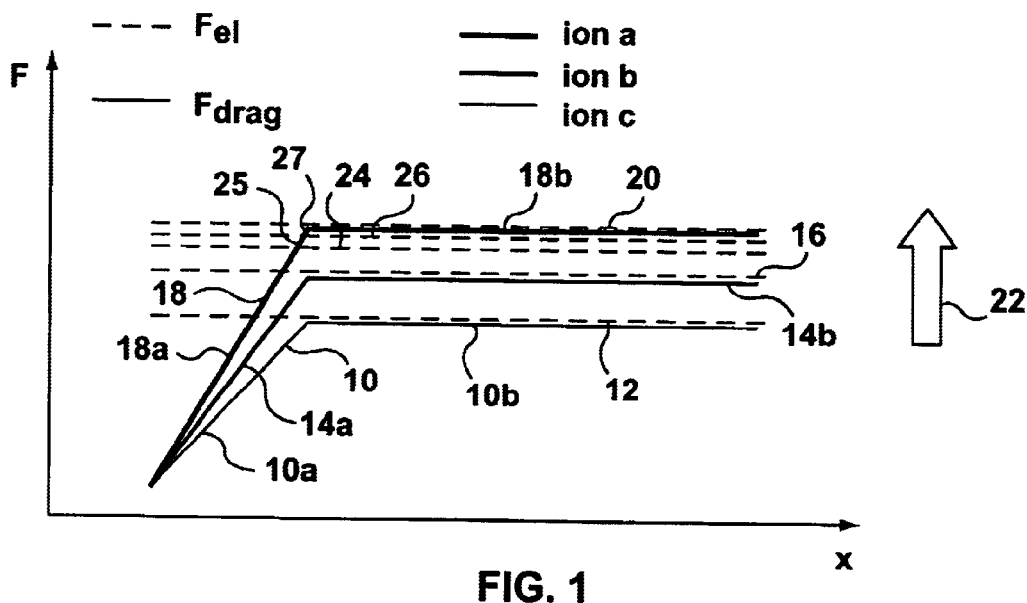
FIG. 1 is a graph showing variation of electric field and gas drag forces along the axis of an ion guide in a first embodiment of the present invention.

Referring first to FIG. 1, this shows all the vertical axis the magnitude of drag force and electric force. The horizontal axis shows distance along the axis of the ion guide from the entrance or inlet at X=0, towards the exit of the ion guide.

Various techniques could be used for generating the axial electric field, and many of these are disclosed in U.S. Pat. No. 5,487,386, mentioned above. In the case of a multipole ion guide, the individual rods can be segmented, to enable the axial field to be generated by applying different DC potentials to the different segments. Alternatively, additional elements can be provided around and between the rods of the multipole rod set, solely for the purpose of generating the axial field. Instead of a multipole ion guide, as disclosed in that U.S. patent, a ring guide can be used, which facilitates generation of an axial field. A further known ion guide is a double helix structure; to generate an axial field along the length of such an ion guide would require techniques similar to those proposed for a multipole rod set, i.e., either some segmented rod structure or separate electrodes for generating the axial field.

Figure 2:
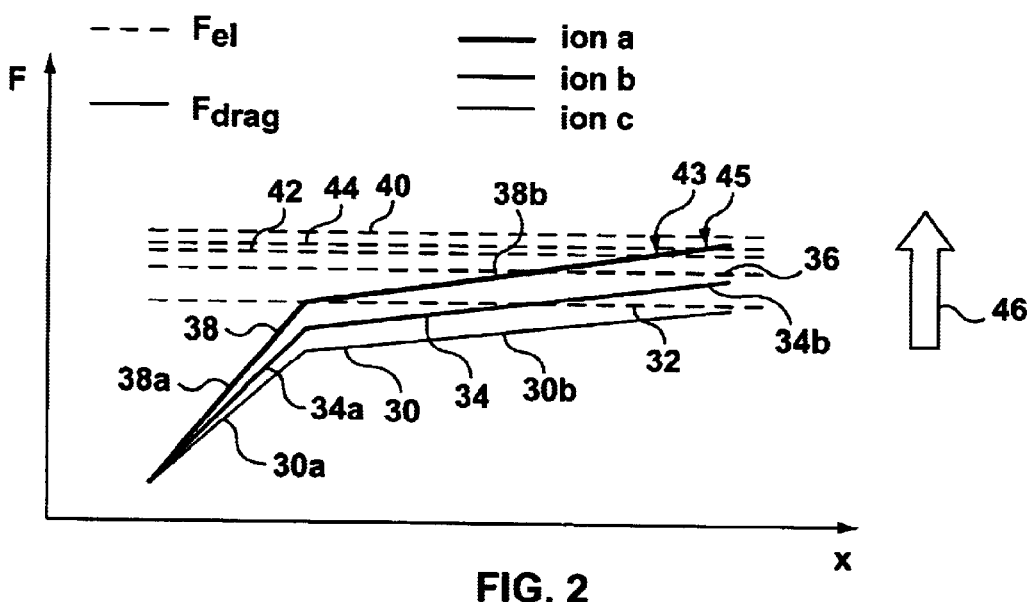
FIG. 2 is a graph showing a variation of electric field and drag forces along the axis of a second embodiment of the present invention.

With respect to generation of the drag force and varying drag force profiles as shown in FIGS. 1 and 2, this can be achieved in various ways. For multipole rod sets, it is conventional to provide some sort of holder holding the rods in alignment and defining a central aperture. To vary the velocity of the gas and hence the drag force, a number of these holders could be provided spaced along the rod set, and each providing an aperture of different cross section. This would then necessarily vary the gas velocity along the axis of the ion guide, as desired.

FIG. 1, and also FIG. 2, are schematic in a number of respects. Firstly, both the lines for the drag force and the electric field force are shown idealized. In practice, it is not expected that such perfect, idealized profiles will be obtained.

In both Figures, a forward electric field is shown by dashed lines and a backward drag force is indicated by a solid line.

A single line 10 is shown representing a profile for the drag force for a particular ion. It will be understood that while this profile will be similar for different ions, its magnitude will vary from ion to ion, and not necessarily in relation to an ion's charge. However, a key aspect to the invention is the relative magnitude of the forces applied by the electric field and the gas drag force.

Thus, FIG. 1 shows an axial drag force, established by a gas flow from the exit of the ion guide towards the entrance thereof at 10. This drag force profile 10 comprises an initial portion 10a where the drag force starts at a low value close to the entrance of the ion guide and increases at a constant rate until it reaches a constant value indicated at 10b. In practice, this can be achieved by providing some sort of vent for the gas close to the entrance, so that the actual gas velocity drops quickly and at a steady rate, as indicated by 10a.

Then, for ions subjected to an axial field indicated at 12, the axial electric field, driving the ions towards the ion guide exit, will exceed the drag force indicated by 10, at any portion of the ion guide. Consequently, the ions will be accelerated significantly in the portion 10a, and once the ions reach the level portion 10b, there will be a constant force tending to accelerate the ions. It will be appreciated that this representation, in another respect is also idealized and schematic. Thus, the drag force will likely depend not just on a particular ion's characteristics, but also its velocity. In other words, as an ion is accelerated, the drag force it experiences will increase, until it balances the force applied by the electric field. In other words, the ions should reach a constant axial velocity in the section indicated at 10b.

The drag force applied by the gas and the force applied by the electric field will vary from ion to ion. In general, the force applied by the electric field is simply a multiple of the electric field strength and the charge on the ion. The characteristics of another ion are indicated at 14, 16. Thus, the drag force 14 again has a first portion 14a with a distinct gradient and a second portion 14b showing a constant or level drag force. When the electric field is set to apply a force indicated at 16, then the ion will be driven through the ion guide and out to the next stage of the instrument.

A further characteristic is indicated by the lines 18,20. This indicates an ion having a relatively high drag force 18, which again shows a first portion 18a and a second portion 18b, where portion 18a shows a distinct gradient and portion 18b is essentially flat. For this ion, the electric field would need to be set to generate an electric field force indicated at 20, in order to cause the ion to be displaced through the ion guide.

To further understand the characteristics of this type of device, additional electric field lines are indicated at 24, 26. When the electric field is applied so as to generate an electric field force indicated by line 24, then this is only sufficient to overcome the drag force at the beginning portion of the ion guide. Thus, ions will be displaced, until the electric field force is balanced by the drag force 18a. This will result in ions being trapped at a location indicated approximately at 25.

When the field is increased further to a value indicated at 26, then ions will be displaced a little further towards the entrance, again until the electric field balances the drag force indicated at 18a. Ions will then be trapped or held at a location indicated at approximately at 27. Thus, it will be appreciated at, as the electric field is progressively increased, as indicated by the arrow 22, and while the electric field is less than the value of the drag force indicated at 18b, then ions will be progressively displaced from the inlet of the ion guide. Once the electric field reaches the level indicated at 20 and exceeds the drag force indicated at 18b, then ions will be moved continuously to the exit of the ion guide.

It will thus be appreciated that this arrangement, in effect, enables ions to be trapped or held at different locations, depending upon their varying charges and mobility characteristics. This enables ions to be separated in the ion guide, and eluted out from the ion guide at different times. This can be achieved by progressively increasing the electric field, and this is indicated, schematically by the arrow 22. Increasing the electric field will cause relative ratios of the electric force profiles 20, 24, and 26 to remain the same, but the magnitude to increase, again relative to the drag force profile 18. Thus, as each electric force profile exceeds the drag force 18b, the ions will be driven along the full length of the ion guide and eluted out of the ion guide. This enables controlled separation of the ions. The rate of change in the electric force field can be varied, and at any time it can be held, to hold already trapped ions in the ion guide.

FIG. 2 shows a generally similar arrangement, but here the drag force profile is indicated at 30 with different portions 30a, 30b. Here, the downstream portion of the drag force profile 30b is not level, but rather shows a progressively increasing magnitude. Corresponding to FIG. 1, an electric force profile is shown at 32. Where this exceeds the largest value of the drag force 30, then ions are driven out of the ion guide.

Like FIG. 1, FIG. 2 also shows profiles for ions with different characteristics. Thus, at 34, there is shown the drag force profile for an ion with greater drag. For such an ion, an electric field force, indicated at 36, is necessary in order to drive such ions through the ion guide.

Correspondingly, an ion with an even greater drag is shown with a drag force profile 38. (Both drag force profiles 34, 38 are again shown with portions 34a, 34b and 38a, 38b, corresponding to the drag force profile 30). For this drag force profile 38, an electrical field force indicated at 40 is required in order to overcome the maximum value of the drag force and to ensure that ions are removed from the ion guide.

Again, corresponding to FIG. 1, the top drag force profile 38 is shown with additional electric field force lines 42, 44 showing the effect of lesser electric fields. For an electric field force 42, when this balances the drag force 38 ions tend to be trapped. This is indicated at the location 43. Correspondingly, when the electric field force is increased further to a value indicated at 44, ions will tend to move further to right, towards the inlet, until the electric and drag forces are again balanced. This is indicated at 45, indicating a location where ions will tend to be held or trapped. When the electric field force is increased further, to the value of 40, then ions will eventually overcome the maximum drag force, and be driven out of the ion guide.

In FIG. 2, since the drag force profile 30b is not level but is inclined, this means that there will be a tendency for all ions to be trapped or held at a certain location, throughout the length of the ion guide.

In both FIGS. 1 and 2, ions are driven out of the ion guide once the electric force exceeds the drag force. In FIG. 1, separation quality is subject to diffusion. Once the electric force matches the drag force indicated at 10b, ions will be affected by diffusion; i.e. ions will tend to diffuse axially, and this will increase the width of the ion packet. Thus, the arrangement of FIG. 1 exhibits some dependence of the quality of separation upon the scan rate.

On the other hand the arrangement of FIG. 2 should not be affected by diffusion to the same extent. By providing a drag force profile that varies along the length of the ion guide, the problem of diffusion should be largely avoided. It can be operated in a mode where separation quality does not depend upon the scan rate and the width of each ion packet is determined by the slope of the drag force 30b.

Figure 3A:
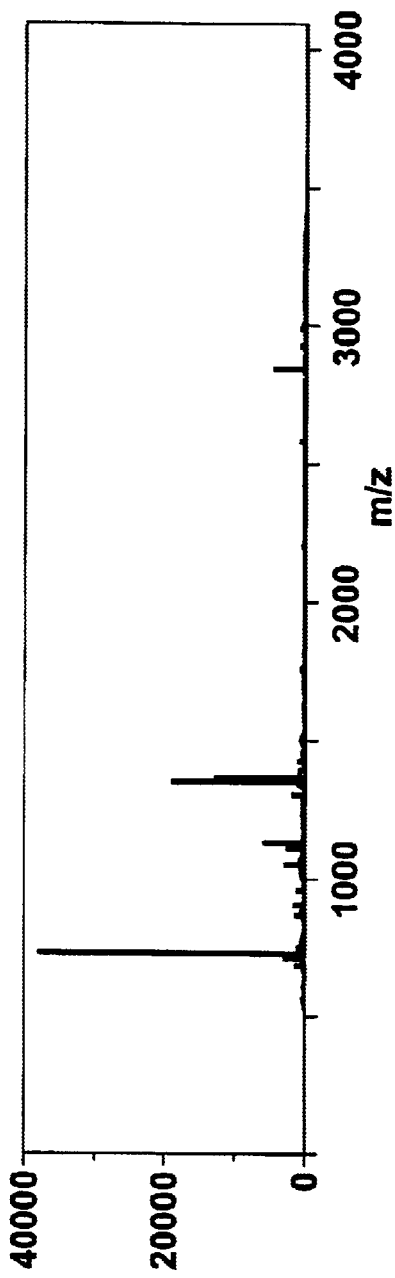
FIG. 3 shows a mass spectrum obtained using the present invention.
Figure 3B:
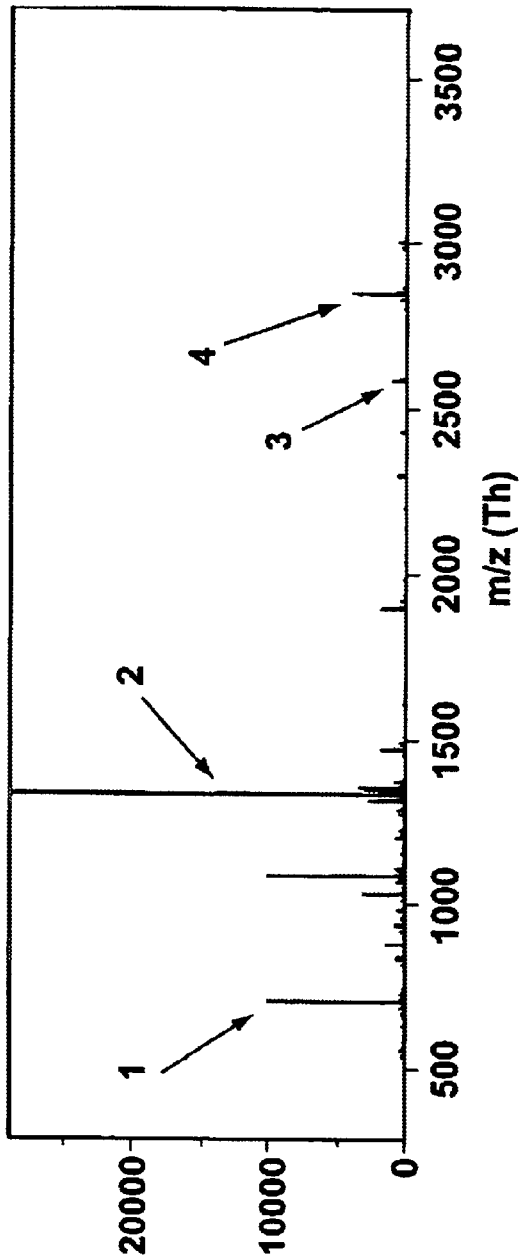
Figure 4A:
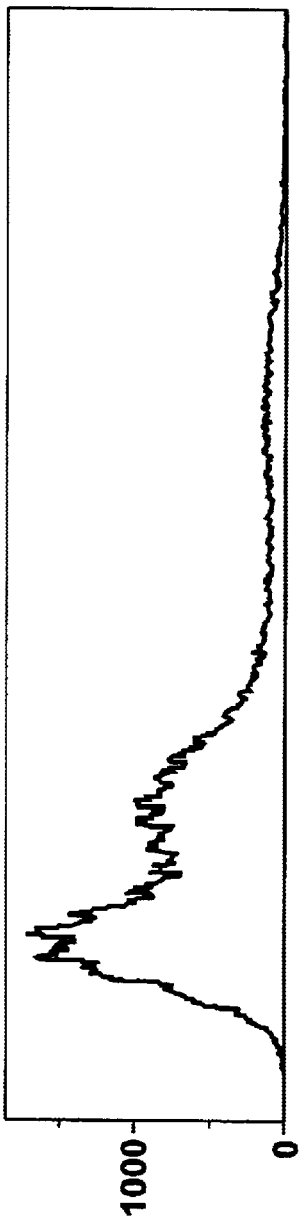
FIG. 4 is a graph showing variation and extraction of time.
Figure 4B:
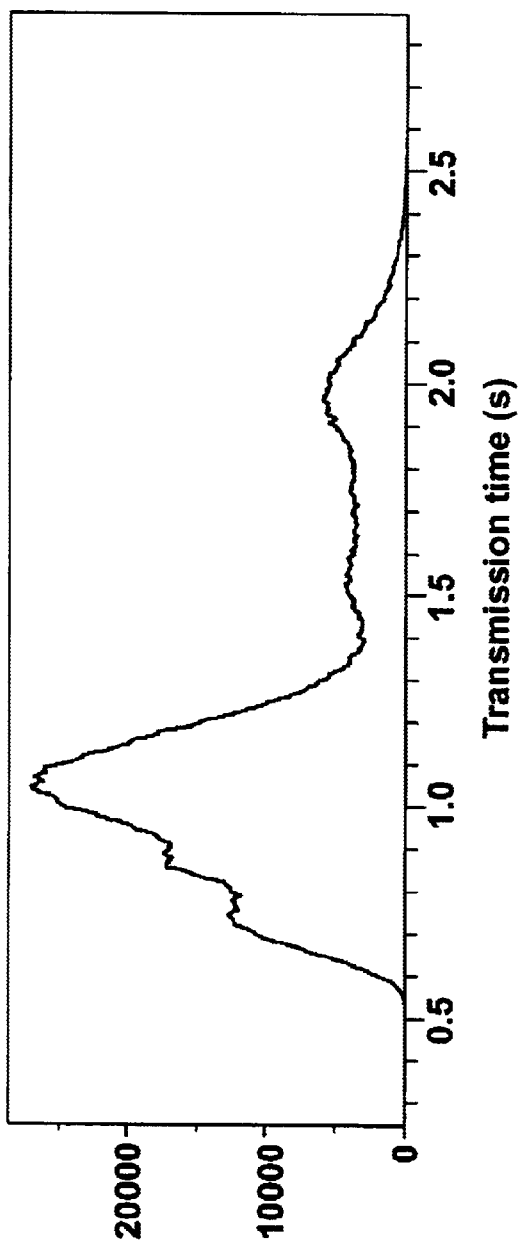
Figure 5A:
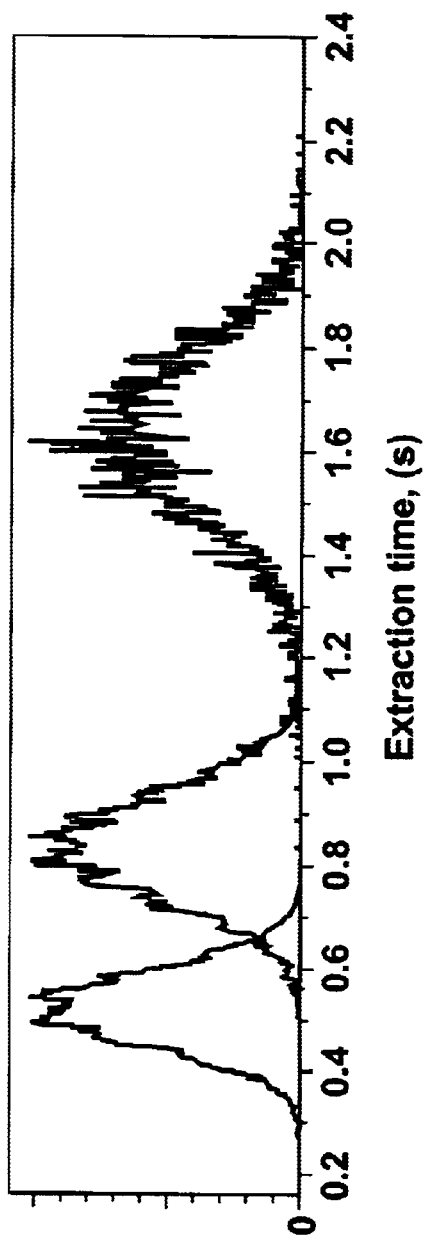
FIG. 5 is a graph similar to FIG. 4 showing a variation extraction time for the three major peaks of FIG. 3.
Figure 5B:
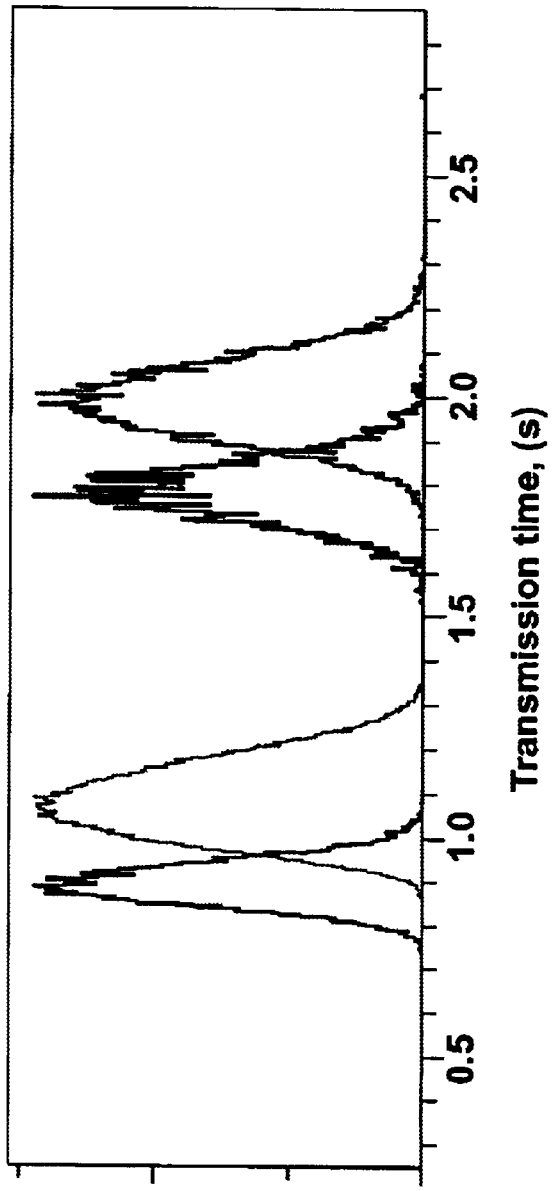

Turning now to FIGS. 3, 4 and 5, these show test results carried out on an instrument comprising a MALDI quadrupole TOF instrument. This has a MALDI ion source, a quadrupole ion guide and a TOF analysis section.

The quadrupole ion guide was a segmented quadrupole ion guide to enable an axial field to be created. The drag force was provided by a gas flow in the opposite direction to the ions. The gas flow profile corresponded to that in FIG. 1, although not exactly, and in particular the profile indicated at 10b was somewhat uneven, due to mechanical constraints of the instrument thereby resulting in resolution that is below the theoretical prediction.

FIG. 3 shows the mass spectrum and shows three peaks at 726.394 m/z, 1347.736 m/z and 2845.762 m/z. FIG. 4 shows the extraction time profile, and as can be seen, there are two relatively early peaks and a later rather more diffuse peak.

FIG. 5 shows the profile of FIG. 4, split to show the three separate peaks, corresponding to the peaks of FIG. 3. Additionally, the three peaks are normalized in FIG. 5. As is common, the peaks with the large m/z have lower mobility and emerge at a later time.

It is to be understood that numerous variations and modifications are possible within the scope of the present invention. Thus, while FIGS. 1 and 2 show a constant profile for the electric field force, this could in fact be varied. Different devices can be used for generating the electric field, and these can be arranged to provide an electric field that varies along the length of the ion guide. Nonetheless, the profile for each ion would be similar, and its magnitude would be determined by the magnitude of the electric field and the charge on each ion.

While FIGS. 1 and 2 show a simple profile for the drag force having just two different sections, it is to be understood that various profiles can be provided, and these could include three or more sections having different characteristics. Similarly, the electric force profile could have three or more different sections each exhibiting different characteristics.

Figure 6:
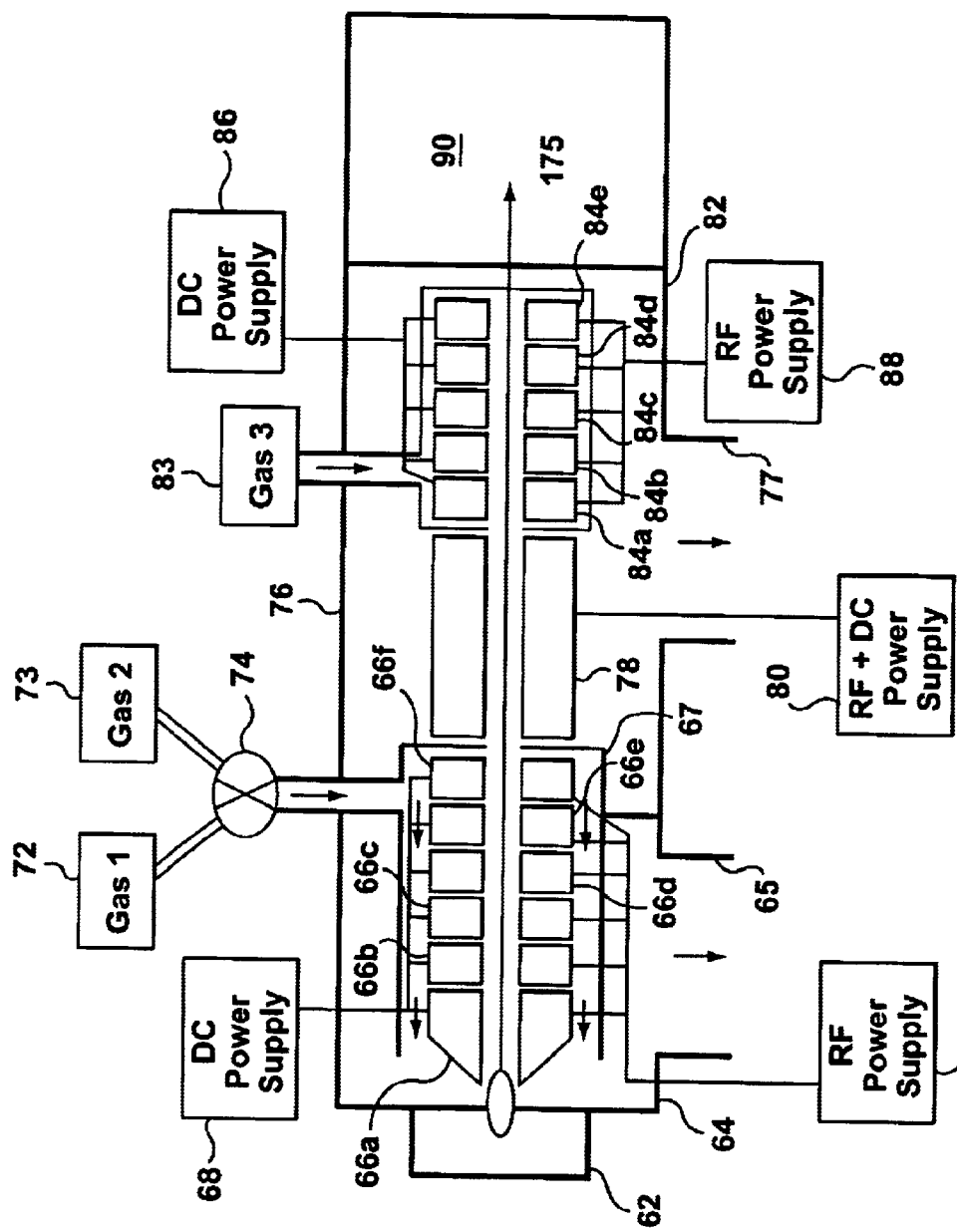
FIG. 6 is a schematic diagram of a mass spectrometer incorporating the present invention and including an IMS section, a fragmentation cell and a mass analysis section.
Figure 7:
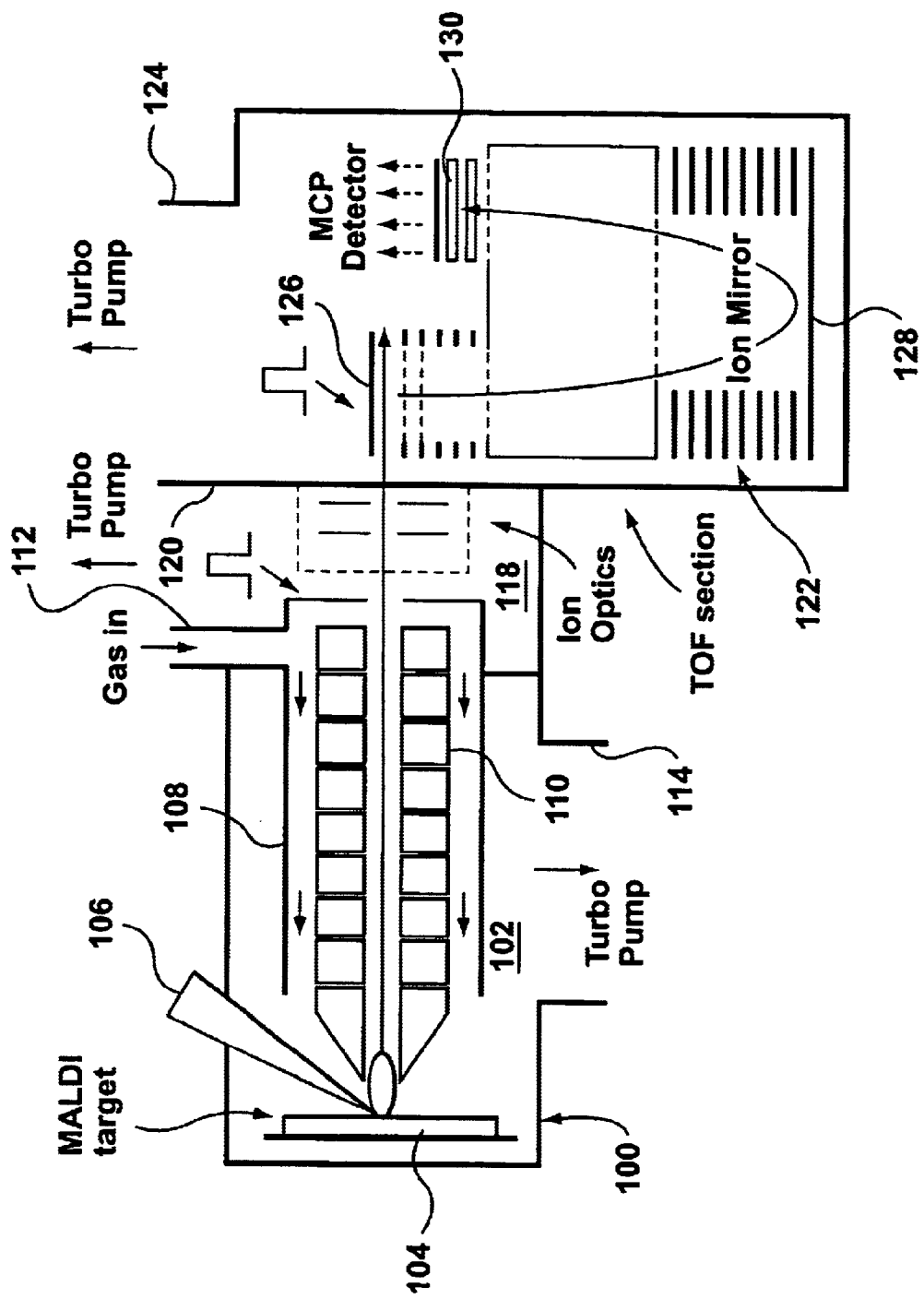
FIG. 7 is a schematic diagram of a mass spectrometer, including an IMS section followed by an orthogonal TOF (Time of Flight) section.

Referring to FIG. 7, this shows a further alternative embodiment of the present invention. This essentially has an IMS section 100 followed by an orthogonal TOF (Time of Flight) section 122. The IMS section 100 defines a chamber 102, within which there is a MALDI target 104. As indicated at 106, the MALDI target would be irradiated to form pulses of ions. These pulses of ions are collected within a segmented, quadrupole rod set indicated at 110. As for the embodiment of FIG. 6, this segmented rod set 110 would have suitable power supplies connected to it to provide RF voltages to provide the ring guide characteristics and DC voltages to generate an axial DC field (presumably no DC resolving voltages). A housing or casing 108 is provided around the quadrupole rod set 110 and is connected to a gas inlet 112. Thus, as before, gas would be supplied and would flow counter to the direction of ion flow, as indicated by the arrows. As the embodiment of FIG. 6, an arrangement can be provided to supply different gases or mixtures of gases. Thus, ions travel through the rods at 110 experiencing a forward axial field and a retarding or backward drag force from the gas flow.

In known manner, the chamber 102 is provided with a connection 114 for connection to a turbo vacuum pump.

Ions exit from the IMS section 100 into an intermediate chamber 118, provided with its own connection 120 to a turbo vacuum pump. This intermediate chamber 118 includes ion optics in known manner.

The ions then pass into the orthogonal TOF section 122. This again includes a standard connection 124 for a turbo vacuum pump.

Within the TOF section 122, there is a standard arrangement of grids 126 for gating the ions and forming pulses of the ions. Here, the TOF section includes an ion mirror 128, and a detector 130.

Thus, in the embodiment of FIG. 7, ions are subject to ion mobility separation in the IMS section 100, generally as described above in relation to FIGS. 1 and 2. Thus, ions are subject to both an electrical field and a drag force from the gas to separate ions, while at the same time being maintained on the axis by the guiding effect of the quadrupole rod set. Providing an RF ion guide enables the ions to have large residence times, without the problems of significant radial diffusion. Large residence times in turn permit desired separation of different types of ions. The ions, then separated based on mobility characteristics, can be subject to separate analysis in the TOF section 122.

While the described embodiments have the electric force arranged to drive the ions forward with the drag force acting as a retarding force, these too could be reversed, i.e. the electric field could provide a retarding force, and the gas flow could provide a force driving ions towards the exit.

Additionally, for both the electric force field and the gas flow, it is possible to provide a mixture of both a forward field and a retarding field along the length of the ion guide. For example, for the electric field, one portion of the ion guide can be provided with a forward field, and another portion of the ion guide could be provided with a backward or a retarding field. Correspondingly, it is conceivable that gas flow could be arranged entering at some middle point of the ion guide, so that the gas flow provides a backward or a retarding field in the first portion of the ion guide and a forward field in the portion of the ion guide adjacent the exit.

The invention offers a number of advantages. The mobility separation provided by the invention may enable MS/MS multiplexing, as shown in the embodiment of FIG. 6, since different precursor ions are eluted at different times. Thus as one group or packet of ions is eluted, it could be subjected to conventional fragmentation in a fragmentation cell and then a second mass analysis step on the fragment ions. While this is carried out, other ions can be retained in the ion guide. Consequently, ions are not wasted, when one or more precursor ions need to be analyzed. This can be applicable to a triple quadrupole configuration or a QqTOF, or any other suitable configuration. It is expected that the sensitivity increase is approximately proportional to the number of peaks of interest that can be analyzed separately.

Reference is also made to my earlier application Ser. No. 10/004,800 filed Dec. 7, 2001, the contents of which are hereby incorporated by reference. In that application, an instrument is proposed having two different types of separation, namely ion mobility separation and conventional mass analysis based on mass to charge ratio. However, in that earlier application, ion mobility separation is effected with, essentially, stagnant gas in known manner. That earlier application notes that such an arrangement provides two dimensions of separation which can be considered as "orthogonal". Thus, for many analytes, the mobility characteristics and the mass to charge characteristics can be independent or orthogonal from one another. This is of particular advantage, where it is desired to separate two ions having identical or very similar mass to charge ratios, preventing adequate separation in a conventional mass spectrometer. These ions may have quite different mobility characteristics, enabling them to be first separated in an ion mobility spectrometer and the two ions, following separation, can be separately subject to a mass analysis step.

At the same time, this earlier application additionally notes that, while these characteristics are orthogonal and independent, they also can show some relationship. Thus, for many ions, larger ions with larger mass to charge ratios commonly show lower drift velocities or larger drift times. This characteristic can be used to optimize the performance of an instrument.

A certain correlation between mobility coefficient and mass to charge ratio allows one to take advantage of the Pulsar mode of operation of orthogonal TOF over a wide mass range, resulting in potentially increased sensitivity, of at least four times in the present instrument. In the Pulsar mode of operation ions are stored and then injected as pulses into an orthogonal injection TOF instrument. This allows ion transmission close to 100% but only for a narrow m/z range while ions outside of this range are being lost.

By first carrying out a mobility separation stage, ions of interest can be delivered sequentially, in time, to the TOF instrument and parameters of the Pulsar mode can be dynamically tuned to optimize transmission of the ions eluting at each particular moment. Here it will be understood that the cycle time of a conventional TOF instrument of the order of 100 $\mu$s is typically much shorter than the time taken for an ion to elute from a mobility section, so that numerous TOF cycles would be required to capture the full range of ions of interest.

At the same time, as each ion will arrive at the TOF section at a different time, the TOF characteristics can be set for each ion. Thus, as noted, there is often some relationship between the m/z ratio and mobility characteristics. The cycle time for the TOF can be set based on the anticipated m/z ratio, again to optimize use of the sample.

Another way to take advantage of the mobility separation can be by using it instead of mass separation for MS/MS experiments. Thus, the first step can be used instead of mass separation for MS/MS experiments. Thus, the first step could be separation of ions based on mobility, rather than mass. It may thus be used to implement some version of "poor man" MS/MS setup. By this it is meant that the ion mobility section can be first used to effect a simple or poor resolution MS step, prior to some subsequent analysis step. This again recognizes that m/z ratio is often linked to mobility characteristics, while at the same time mobility separation usually shows relatively poor resolution. For some purposes, the poor resolution, at least in the first stage, may be more than adequate. This has the advantage that complex and expensive electronic circuitry for the first MS section can be eliminated, as the electronics for a TOF section are relatively simple.

Mobility separation can simplify analysis of some mixtures, to at least some extent. This is due to the fact that mobility characteristics of ions are entirely separate from the mass to charge ratio. Thus, mobility separation may enable the separation of ions which cannot be adequately separated only by the mass to charge ratio. This in turn enables analysis to be simplified.

Reference will now be made to FIG. 6, which shows an embodiment of a mass spectrometer incorporating the present invention, and indicated generally by the reference 60. The Mass spectrometer has a configuration commonly identified as a tandem mass spectrometer, in that it has a mass selection section, followed by a fragmentation cell and then a further mass resolving section. This further mass resolving section can be any suitable analyzer including a quadrupole rod set and detector or a Time of Flight (TOF) section for analyzing fragments from the fragmentation cell. An orthogonal TOF section is, one possible arrangement for the final mass analysis section. Additionally, in accordance with the present invention, there is an IMS section upstream of the first mass selection section.

An ion source 62 generates ions and the ions are admitted into the mobility section (IMS), identified at 64.

This IMS section 64 has a rod set 66, which comprises a plurality of rod segments 66a, 66b etc., as in U.S. Pat. No. 5,847,386. The number of rod segments can vary, and for simplicity only a few are shown in FIG. 6. It is anticipated that the number of rod segments can be 10, 20, 60 or even higher. The length of the IMS section 64 can be varied as desired. Currently, the inventor is proposing an IMS section 64 that is 12 inches long, but a longer IMS section, for example 24 inches, would give better separation by the IMS technique.

A DC power supply 68 is connected to the various rod segments of the rod set 66, to generate a potential gradient, somewhat as shown in FIG. 2. Again, an RF power supply 70 is connected to the various segments of the rod set 66, for guiding and focusing ions through the ion mobility section 64.

Two gas supplies are provided as indicated at 72, 73, and these are connected to a mixing valve 74 that enables both the proportions of the two gases, and the total gas flow to be regulated. The IMS section 64 is maintained at a pressure in the range of 1 m Torr to 10 Torr. Lower pressures are impractical for mobility separation and at higher pressures the collisional focusing effect is reduced. The gas source is shown schematically, and in order to establish the necessary gas flow, it is introduced at one end of a housing 67 around the IMS section 64, with one or more exhausts or vents along the length of the IMS section 64, to establish the desired gas velocity profile. As mentioned, profiles of supports for the rod segments can provide varying internal apertures, to vary the gas velocity as desired.

The IMS section 64 can be filled with any suitable gas, e.g., nitrogen, hydrogen, argon, helium (although hydrogen and helium may be impractical due to some pumping limitations of modern vacuum pumps). Oxygen and carbon dioxide could also be used, and in general it is believed that any of the noble gases could be used. $SF_6$ is another possible gas, and for some applications, it has the advantage that it has a strong affinity for electrons.

The reason for providing two gases is that the mobility characteristics for ions of interest can vary between different gases. For example, for two or more different ions of interest, it may be that all the ions have similar mobilities in one gas, but quite different mobilities in another gas. Thus, by switching to the other gas, separation can be achieved. In some cases, it may be desirable to use a mixture of two or more gases.

From the IMS section 64, ions pass into a mass selection section 76, which here is shown including a quadrupole rod set 78. A power supply 80 is shown connected to the rod set 78. The power supply 80 can be a conventional RF and DC power supply for supplying a signal to the rod set, to select an ion with an m/z ratio of interest. In known manner a desired resolution can be set for the rod set 78. The mass selection section 76 serves to clean up ions selected by mobility separation in the IMS section 64. Resolution in the IMS section 64 will usually be in the range of 20 to 100, whereas resolution of the order of 1000 is routine in a true MS section.

Downstream from the mass selection section 76, there is a fragmentation cell 82. In known manner, the fragmentation cell 82 is located in the same chamber as the rod set 78. Connections to turbo vacuum groups, again conventional, are indicated at 65, 77. The fragmentation cell includes a gas source 83, and pressure within the fragmentation cell 82 can be controlled in known manner. The fragmentation cell 82 has its own segmented rod set 84, which again includes a plurality of rod segments 84a, 84b etc. Use of a segmented rod set in this manner can follow that described in U.S. Pat. No. 5,847,386. Additionally, following the present invention, rather than just provide a static collision gas in the fragmentation cell 82, as for the IMS section 64, provision can be made to provide the gas with a velocity in a chosen direction; it is also possible that this velocity could vary in magnitude along the length of the fragmentation cell and the direction of the gas flow could vary between different sections of the fragmentation cell 82. For this purpose, inlets and outlets for the gas would be provided where required. The fragmentation cell 82 can use Collision Induced Dissociation (CID) to cause fragmentation. Alternatively, fragmentation methods different from Collision Induced Dissociation (CID) can be implemented in the fragmentation cell 82. Such methods may include surface induced dissociation (SID), infrared multi-photon dissociation (IRMPD) or other suitable methods of ion fragmentation.

Again, respective power supplies 86 and 88 are provided for a DC signal to establish a potential gradient through the rod set 84, and an RF field respectively. The power supply 88 can additionally supply some resolving DC component if it is desired to operate the fragmentation cell in a band pass mode, as described in International Patent Application PCT/CA98/00536.

Finally, the fragmentation cell 82 is connected to a final mass analyzer 90, that can be conventional, and details are not shown.

This arrangement of FIG. 6 is expected to provide an increased performance in MS/MS scans and the like. In effect, in addition to a first MS (mass selection) step, effected in the mass selection section 76, ions are previously subjected to IMS separation in the IMS section 64. The second mass selection (MS) step occurs in the section 90.

This can have the advantage of cleaning up a parent ion peak. Often, for a parent ion peak selected in the mass selection section 76, there will be various interfering peaks of ions that have similar, or even identical, m/z ratios. These cannot be distinguished by mass selection alone. The IMS section 64 thus has the advantage of enabling separation of these various interfering ions, by their different mobility characteristics. Thus, knowing both the m/z ratio of a parent ion and its mobility characteristics, the parent ions can be taken from the IMS section 64 at the appropriate time, with ions having lesser and greater mobilities being rejected. These parent ions are then subjected to further mass selection in section 76, which principally will ensure elimination of any ions which have accidentally been carried over and ions which have similar IMS characteristics but quite different m/z ratios.

Then, as is conventional, the selected parent ions will be passed into the fragmentation cell 82 for fragmentation. As detailed in U.S. Pat. No. 5,847,386, the potential gradient maintained through the rod set 84 will ensure that the parent fragment ions travel through the fragmentation cell 82 in a reasonable time, and no lengthy time will be needed to enable any "tail" to clear from the fragmentation cell 82. Additionally, the potential gradient maintains the velocity of the parent ions, to ensure good fragmentation efficiency. Thus, if any parent ions are subjected to glancing collisions, tending to reduce their kinetic energy without fragmenting the ions, they are then further accelerated until fragmentation does occur.

The fragment ions and any unfragmented parent ions then pass through to the final mass analyzer 90, for analysis of the fragments, again in known manner.

The arrangement or apparatus of FIG. 6 resembles a traditional tandem mass spectrometer, for example a quadrupole time of flight tandem mass QqTOF spectrometer. Such an instrument has several modes of operation as described in [Morris H., Paxton T., Dell A., Langhorne J., Berg M., Bordoli R., Hoyes J., Bateman R.; *Rapid Commun. Mass Spectrom.*, 10, 889, (1996). Shevchenko A., Chernushevich I., Spicer V., Ens W., Standing K., Thomson B., Wilm M., Mann M.; *Rapid Commun. Mass Spectrom.*, 1997, 11, 1015–1025]. An additional feature is that mobility separation allows one to increase sensitivity of such an instrument in different modes of operation. In the single MS mode (overall spectrum analysis) the sensitivity can be improved by using variable frequency scanning and/or bunching.

In MS/MS mode (fragment ion spectrum of a selected precursor) the sensitivity of the setup FIG. 6 can be further improved using parent ion multiplexing. Traditional QqTOF mass spectrometer can only select one precursor ion at a time, this represents a significant loss of sensitivity when analyzing mixtures containing more than one precursor ion of interest. Use of mobility separation in section 64 will produce a sequence of different precursor ions "eluting" out of the mobility stage. The quadrupole mass selector 76 can be tuned to the precursor ion of interest "eluting" at the moment. Thus, many precursor ions can be selected in the quadrupole 76, fragmented in the fragmentation cell 82 and analyzed in the TOF 90 during the course of one experiment. This gives better use of a sample and does not require other precursors to be rejected while another precursor of interest is being analyzed.

For the "poor man" configuration, detailed above, the MS selection section 76 would be eliminated. This then gives the possibility of combining the IMS section 64 and the fragmentation cell 82. In effect one continuous rod set could be provided extending through both sections.

What is claimed is:

1. A method of separating ions, the method comprising:
    a) supplying ions to a radio frequency ion guide;
    b) applying an axial electric field to provide a force in one direction along the axis of the ion guide;
    c) providing a gas flow along the ion guide to provide a drag force on ions opposing the force provided by the electric field.

2. A method as claimed in claim 1, the method including an additional step:
    d) initially setting the electric field and the gas flow such that for at least some ions the force of the electric field and the drag force provided by the gas flow balance one another, to retain the ions within the ion guide, and subsequently adjusting at least one of the electric field and the gas flow to cause desired ions to elute from the ion guide.

3. A method as claimed in claim 2, which includes setting the electric field and the gas flow to separate different ions based on ion mobility and charge characteristics, and, in step (d), progressively altering at least one of the electric field and the gas flow to cause different packets of desired ions to elute sequentially from the ion guide.

4. A method as claimed in claim 3, which includes setting of the electric field to provide a backward force driving ions away from the exit of the ion guide and setting the gas flow to provide a drag.force driving ions towards the exit of the ion guide, and wherein step (d) includes at least one of the progressively increasing the magnitude of the gas flow and progressively decreasing the magnitude of the electric field, to cause desired packets of ions to sequentially elute from the ion guide.

5. A method as claimed in claim 1 or 2 which includes, in at least one portion of the ion guide, setting the electric field to provide a force driving ions towards the exit of the ion guide and setting the gas flow to provide a backward drag force driving ions away from the exit of the ion guide, and wherein step (d) comprises a progressively increasing the magnitude of the electric field.

6. A method as claimed in claim 5, which includes providing an electric field which is constant along the length of the ion guide, and providing a gas flow having a first portion adjacent the inlet of the ion guide that provides a drag force progressively increasing in magnitude from the inlet of the ion guide, and a second portion that provides a drag force at least equal to the magnitude of the drag force of the first portion.

7. A method as claimed in claim 6, wherein the drag force provided by the gas flow in the second portion progressively increases towards the exit of the ion guide and increases at a slower rate than the increase in the drag force in the first portion.

8. A method as claimed in claim 2, which includes the following additional step:
    (e) passing ions eluted from the ion guide into a fragmentation cell, to effect at least one of reaction and fragmentation of the ions, to generate product ions.

9. A method as claimed in claim 8, which includes the additional step:
    (f) passing the product ions into a mass analyzer for mass analysis.

10. A method as claimed in claim 9, which includes passing the product ions into a time-of-flight section for mass analysis.

11. A method as claimed in claim 9, which includes, prior to step (e), passing ions from the ion guide through a mass selection section to select desired parent ions.

12. A method as claimed in claim 10 or 11, which includes, in the fragmentation cell, providing a gas flow along the fragmentation cell and an electric field along the fragmentation cell, and controlling the electric field and the gas flow to trap ions within the fragmentation cell and to control elution of ions from the fragmentation cell into the time-of-flight mass spectrometer, and timing elution of ions from the fragmentation cell with analysis cycles in the TOF section, thereby to enhance sensitivity.

13. A method as claimed in claim 8, which includes providing a first quadrupole rod set as the ion guide and providing the fragmentation cell with a second quadrupole rod set and forming an axial electric field along the axis of both of the first and second quadrupole rod sets.

14. A method as claimed in claim 13, which includes providing both of the first and second quadrupole rod sets as segmented rod sets and supplying different DC voltages to the segments of a first quadrupole rod set and different DC voltages to the segments of a second quadrupole rod set, to generate the axial electric fields.

15. A method as claimed in claim 13, which includes providing first additional electrodes for the first quadrupole rod set and second additional electrodes for the second quadrupole rod set, and applying voltages to the first and second additional electrodes to generate the axial electric fields.

16. A method as claimed in claim 8, which includes effecting fragmentation by one of collionally induced dissociation (CID), surface induced dissociation (SID), and infrared multi-photon dissociation (IRMPD).

17. A method as claimed in claim 2, which includes providing a quadrupole rod set as the ion guide and providing an axial electric field along the quadrupole rod set.

18. A method as claimed in claim 17, which includes providing the quadrupole rod set as a segmented rod set and providing different DC voltages to the segments of each rod, thereby to generate an axial electric field along the length of the ion guide.

19. A method as claimed in claim 17, which includes providing additional electrodes for generating the axial electric field and supplying voltages to the additional electrodes to generate the axial electric field.

20. An apparatus for separating ions, the apparatus comprising:
    an ion guide;
    means for generating an electric field along the length of the ion guide; and
    means for supplying gas to at least one location of the ion guide and for exhausting gas from at least one other location of the ion guide, to generate a desired gas velocity profile along the ion guide, whereby, in use, movement of ions along the ion guide is dependent upon both an electric field force and a drag force applied to the ions.

21. An apparatus as claimed in claim 20, wherein the ion guide comprises a plurality of rods forming a multipole ion guide, and wherein each rod is segmented, and the means for generating an electric field comprises a power source connected to the segmented rods, for applying varying potentials to the rod segments.

22. An apparatus as claimed in claim 21, wherein the ion guide forms an ion mobility section, and wherein the apparatus further includes a fragmentation cell connected to the ion mobility section, for effecting at least one of reaction and fragmentation of ions to generate product ions and a final mass analyzer connected to the fragmentation cell for analyzing the product ions.

23. An apparatus as claimed in claim 22, which includes a further mass analyzer interposed between the ion mobility section and the fragmentation cell.

24. An apparatus as claimed in claim 22 or 23, wherein the radio frequency ion guide comprises a first quadrupole rod set and a first power source for applying at least RF voltages to the first quadrupole rod set.

25. An apparatus as claimed in claim 22 or 23, wherein the fragmentation cell includes a multipole rod set having a plurality of rods, wherein the rods thereof are segmented, wherein the fragmentation cell includes a power source connected to the segmented rods for applying varying potentials thereto to generate an electric field along the fragmentation cell, and wherein the fragmentation cell includes means for supplying gas to and venting gas from the fragmentation cell at different locations, to generate a desired gas velocity profile along the length of the fragmentation cell.

26. An apparatus as claimed in claim 25, wherein the means for generating an electric field along the length of the ion guide comprises segmentation of the first multipole rod set into a plurality of segments and a DC power supply connected to the segments of the first multipole rod set, to apply different DC voltages along the length of the first multipole rod set, thereby to generate the electric field and wherein the second multipole rod set comprises a segmented rod set and a second DC power source is connected to the segments of the second multipole rod set, to generate an axial field along the length thereof.

27. An apparatus as claimed in claim 25, wherein the means for generating an electric field along the length of the ion guide comprises a set of first auxiliary electrodes positioned around the first multipole rod set and a first, auxiliary power source connected thereto, for generating the electric field, and wherein, for the fragmentation cell, a plurality of second auxiliary electrodes are positioned around the second multipole rod set, and a second auxiliary power supply is connected thereto, for generating an axial electric field along the length of the fragmentation cell.

28. An apparatus as claimed in claim 25, wherein the final mass analyzer comprises a time-of-flight section.

29. A method of separating ions, the method comprising:
   a) supplying ions to an ion guide;
   b) applying an axial electric field to provide a force in one direction along the axis of the ion guide;
   c) providing a gas flow along the ion guide to provide a drag force on ions opposing the force provided by the electric field;
   d) initially setting the electric field and the gas flow such that for at least some ions the force of the electric field and the drag force provided by the gas flow balance one another, to retain the ions within the ion guide, and subsequently adjusting at least one of the electric field and the gas flow to cause desired ions to elute from the ion guide.

* * * * *

UNITED STATES PATENT AND TRADEMARK OFFICE
CERTIFICATE OF CORRECTION

PATENT NO. : 6,630,662 B1 Page 1 of 1
DATED : October 7, 2003
INVENTOR(S) : Alexandre V. Loboda It is certified that error appears in the above-identified patent and that said Letters Patent is hereby corrected as shown below:

Title page,
Item [73], Assignee, correct to read -- MDS Inc., doing business as MDS Sciex --; and correct address to read -- Concord --.

Signed and Sealed this

Eighteenth Day of May, 2004

JON W. DUDAS
*Acting Director of the United States Patent and Trademark Office*